United States Patent [19]

Hanahan

[11] Patent Number: 4,851,348

[45] Date of Patent: Jul. 25, 1989

[54] BIOLOGICALLY PURE ESCHERICHIA COLI CELL LINE WHICH IS A DEOR⁻ MUTANT AND WHICH IS MORE TRANSFORMATION EFFICIENT WITH FOREIGN PLASMIDS THAN DEOR+ ESCHERICHIA COLI CELL LINES, PROCESSES FOR OBTAINING THESE CELL LINES, METHODS OF USE AND TRANSFORMANTS THEREOF

[75] Inventor: Douglas Hanahan, Cold Spring Harbor, N.Y.

[73] Assignee: Cold Spring Harbor Laboratory, Cold Spring Harbor, N.Y.

[21] Appl. No.: 886,980

[22] Filed: Jul. 16, 1986

[51] Int. Cl.$^4$ .................... C12R 1/185; C12R 1/19; C12N 15/00

[52] U.S. Cl. .................... 435/252.33; 435/172.1; 435/849

[58] Field of Search .................. 435/172.1, 849, 253, 435/252.33

[56] References Cited

PUBLICATIONS

Munch-Petersen, A. et al, Eur. J. Biochem, vol. 27, pp. 208-215, (1972).
Hanahan, J. Mol. Biol., vol. 166, pp. 557-580, (1983).

Primary Examiner—Thomas G. Wiseman
Assistant Examiner—Joan Ellis
Attorney, Agent, or Firm—Felfe & Lynch

[57] ABSTRACT

A method for obtaining *E. coli* cell lines which carry the deoR mutation is described, as well as the cell lines themselves. These cell lines are useful in cell transfection and transformation, as they transfect transform at much higher frequencies than the previously available cell lines.

15 Claims, No Drawings

BIOLOGICALLY PURE ESCHERICHIA COLI CELL LINE WHICH IS A DEOR⁻ MUTANT AND WHICH IS MORE TRANSFORMATION EFFICIENT WITH FOREIGN PLASMIDS THAN DEOR⁺ ESCHERICHIA COLI CELL LINES, PROCESSES FOR OBTAINING THESE CELL LINES, METHODS OF USE

FIELD OF THE INVENTION

This invention relates to novel cell lines (or strains) of Escherichia coli with enhanced properties as a transformation host for DNA, as well as methods for producing said cell lines.

BACKGROUND AND PRIOR ART

The ability to transfer plasmids into E. coli has come to be an integral part of the repertoire of tools used in molecular biology. Plasmid transformation of E. coli was first observed by Cohen, et al, Proc. Natl. Acad. Sci. 69: 2110 (1972), by applying the observation of Mandel, et al, J. Mol. Biol. 53: 159 (1970) that E. coli and bacteriophage λ, when combined in $CaCl_2$ containing solutions at 0° C. caused transfection of the E. coli with the phage.

Much work has been undertaken since then, with the goals of improving transformation frequency, and characterizing the parameters involved. Examples of this work include Hanahan, J. Mol. Biol. 166: 557-580 (1983), which is incorporated by reference herein; Bergmans, et al, J. Bacteriol 146: 564 (1981); Jones, et al, J. Bacteriol 146: 841 (1981); Norgard, et al, Gene 3: 279 (1978).

What the art as a whole teaches, in summary, is that E. coli and DNA interact at low temperatures in an environment containing divalent cations. Many factors improve transformation frequency, including heat shock, inclusion of monovalent cations in the transforming buffer, the addition of hexamine cobalt chloride, treatment with solvents and sulfhydryl reagents, and growth in media containing elevated magnesium levels. These treatments have improved transformation from 1 plasmid in $10^5$ cells, to up to 1 in $10^2$ cells.

One cell line which has been of particular use in this regard is cell line DH-1, which is described in Hanahan, J. Mol. Biol. 166: 557-580 (1983). This cell line is an E. coli mutant (recAI), and has served as a host for, e.g., cDNA cloning, plasmid rescue, and cloning of large DNA fragments.

Recently, it has been learned that a mutation, identified as deoR, can be induced in E. coli cells. When present, the cells which carry the mutant serve as unexpectedly better hosts for all of the techniques described supra, as compared to DH-1. The DH-1 cell line itself has been mutated to contain the deoR mutation, and the resulting cell line is known as DH-5.

Cell line DH-5 has been deposited with the American Type Culture Collection, 12301 Parklawn Drive, Rockville Maryland and bears accession number 53868. This deposit affords permanency of cell line and provides ready access to the public.

A method for obtaining deoR mutated E. coli cell lines, the mutated cell lines themselves, and methods of using these for, e.g., cell transformation, are the subject of this invention.

While the deoR mutations might occur in nature, substantially pure cultures of these have never before been available. The inventions described herein provides a method to one skilled in the art whereby a regular source of the mutant line now becomes available.

DETAILED DESCRIPTION OF PREFERRED EMBODIMENTS

General Protocol for Obtaining deoR Mutations

The deoR mutation involves a gene which encodes a repressor protein. This repressor suppresses the expression of a set of genes involved in nucleotide utilization. In the absence of this protein, the regulated genes are expressed constitutively. When the repressor is absent, as it is in deoR mutations, colonies of the mutants grow more rapidly than non-mutants on inosine containing medium. Inosine is a nucleotide which does not induce derepression of the coordinated genes in question, as do other nucleotides. Munch-Peterson, et al, Eur. J. Biochem 27: 208-215 (1972).

To select for the deoR mutant, whether arising naturally or by, e.g., chemical radiation, or genetically induced mutation, the subject cell sample is inoculated ($10^4$ to $10^5$ cells) into SynIn medum. SynIn medium consists of 10 mM NaCl, 10 mM $NH_4Cl$, 1 mM $MgSO_4 \cdot 7H_2O$, 2.5 mM $K_2HPO_4$, 0.1 mg/ml thiamine, and 1.5 mg/ml Inosine. When used in Agar plates, 1.5% Bacto-Agar is added. For Syn-Adenosine Medium or plates, adenosine replaces inosine.

5-50 ml of cell sample is used, depending upon the mutagenization protocol. When naturally occurring mutants are to be selected, larger amounts of sample should be used, while smaller amounts (5-10 ml) are appropriate for induced mutations.

Cells are cultured at 37° C. with agitation until confluency is reached ($10^9$ cells/ml), and then 50 μl of cells are taken into 5 mls of fresh SynIn medium, and cultured at 37° C. until confluency is reached.

The cycle described supra is repeated 2-5 times, with confluency requiring less and less time, because normal cells will be overgrown by deoR mutations.

Serial dilutions of the cells are then plated into SynIn agar plates, and these are incubated at 37° C. to produce colonies. deoR colonies are noticeably larger.

Candidate deoR cells are then streaked on fresh SynIn plates, together with parenteral deoR⁺ cells. Incubation is at 37° C. deoR colonies appear much faster.

The foregoing protocol was used on E. coli cell line DH1, which is described in Hanahan, J. Mol. Biol 166: 557-580 (1983) but can be used on any E. coli cell line.

In the examples that follow, deoR mutant cell line DH-5 was used, although one skilled in the art will recognize the applicability of the protocols and experiments set forth herein to any E. coli cell line.

EXAMPLE I

Preparation And Isolation of Cell Line DH 5

A sample of E. coli cell line DH 1 was mutagenized with nitrosoguanidine, following the protocol set forth in Miller, Experiments in Molecular Genetics (1972). These mutagenized cells were grown in a minimal essential medium which contained either uridine or inosine. These nucleosides were used as carbon sources because of the observation that cytR and deoR mutant cell lines could be discerned in mixed cell cultures due to the higher growth rate of the mutants on these media (cytR on uridine, deoR on inosine).

After the cells were grown for a relatively long period of time, samples were either streaked on plates, or studied in liquid medium to determine their rate of growth on either uridine or inosine containing media. The results are set forth in following Table 1:

TABLE 1 cytR and deoR mutants
Selection of Mutants

| Sample | Liquid Medium Serial passages | Plate Medium | Uridine | Assay of cloned cells by growth on plate containing Inosine |
|---|---|---|---|---|
| 1 | Ur | Ur | f | f |
| 2 | Ur | In | f | f |
| 3 | Ur | In | mf | mf |
| 4 | In | Ur | f | m |
| 5 | In | Ur | m | m |
| 6 | In | Ur | m | m |
| 7 | In | In | m | f |
| 8 | In | In | m | m |
| 9 | In | In | m | m |
| 10 | In | In | m | m |
| 11 | In | In | s | vf |
| 12 | In | In | m | f |
| DH 1 | | | vs | vs | f = fast
s = slow
vf = very fast
vs = very slow
m = medium

Cell sample 11, it will be seen, grows very fast on inosine containing medium, and slowly on uridine containing medium. This is indicative of the presence of a deoR mutation, and the absence of cytR. This colony was selected as cell line DH 5. Addtional cell lines, which are referred to infra, are DH-4 (cytR, but not deoR), and DH 6 (both cytR and deoR).

EXAMPLE II

Transfection With Plasmids

Additional experiments were performed to determine the rate of transfection with various plasmids. In these experiments, plasmids pBR322, pXAD, and p66 which is a 66 kilobase plasmid composed of human B globin gene sequences inserted into pBR322, were used. These are derivative plasmids of pBR322, which are known to the skilled artisan. See, e.g., Hanahan, supra which also sets forth the protocols used for the transformation experiments. The results are set forth in terms of colony forming units, for two separate runs on each cell line.

| Plasmid | Plate [%] | Cell line | CFU | (Avg) |
|---|---|---|---|---|
| 10 pg pBR322 | 1% | DH 1 | 31,41 | 36 |
| | | DH 4 | 50,34 | 42 |
| | | DH 5 | 80,90 | 85 |
| | | DH 6 | 70,50 | 60 |
| 200 pg pXAD | 2% | DH 1 | 24,26 | 25 |
| | | DH 4 | 40,34 | 37 |
| | | DH 5 | 58,68 | 63 |
| | | DH 6 | 58,70 | 64 |
| 500 pg p66 | 15% | DH 1 | 2,0 | 1 |
| | | DH 4 | 0,0 | 0 |
| | | DH 5 | 3,3 | 3 |
| | | DH 6 | 5,4 | 4 |
| 10 pg pBR322 + DMSO | | DH 5 | 85 | |
| pBR322 (no DMSO) | | DH 5 | 31,37 | 34 |
| pBR322 + DMSO | | DH 6 | 60 | |
| pBR322 (no DMSO) | | DH 6 | 22,28 | 25 |

Clearly, DH 5, an example of a deoR mutant, is showing transfection far in excess of other mutants, and especially in excess of the preferred cell line for transformation, DH-1. DH6 transforms similarly, as it also carries the deoR mutation.

EXAMPLE III

Comparison of DH1 and deoR mutant (DH5)

The cell cultures of DH1 and DH5, described supra, were used in comparative tests. pBR322 and p66 were used as well as a preparation of cDNA ligated into the vector pUC8 (in 20:1 mass ratio of cDNA to vector), at 5ng, 2.5ng, 1.25ng, and 0.5ng concentrations, as well as pUC9 +cDNA at the same amounts. pUC8 + pUC 9 are described in the art.

The cDNA used was RI-SalI DNA fragments from rat muscle. Additionally, as controls, 10pg pBR322 and 1ng p66 were used. The results of these experiments are set forth as follows:

| | DH1 | | DH5 | |
|---|---|---|---|---|
| | 1% | 10% | 1% | 10% |
| 10 pg pBR322 | 20,20 | — | 50,60 | — |
| 1 ng p66 | — | 2,4 | — | 30,40 |
| Frequency of pBR322 transformation (as colonies formed per microgram of DNA) | | $2 \times 10^8$ | | $5.5 \times 10^8$ |
| 0.5 ng pUC8 | 7 | 51 | 17 | 160 |
| 1.25 ng pUC8 | 16 | 70 | 32 | 207 |
| 2.5 ng pUC8 | 7 | 82 | 32 | 284 |
| 5.0 ng pUC8 | 18 | 145 | 64 | 550 |
| 0.5 ng pUC9 | 2 | 21 | 5 | 92 |
| 1.25 ng pUC9 | 3 | 40 | 23 | 120 |
| 2.5 ng pUC9 | 2 | 48 | 24 | 180 |
| 5.0 ng pUC9 | 10 | 90 | 35 | 340 |

Yet again, it can be seen that DH5 is tranformed by all of the plasmids used at rates 3 and 4 times greater than those for DH1. As the only difference in the experimental parameters was the use of DH5 as compared to DH1, clearly the improvement resides in the deoR mutation.

EXAMPLE IV

Another set of experiments were performed using 30 mls of cultured cells, as described supra, in which the various plasmids described, supra, were used. These results were as follows:

| Plasmid | | CFUs | AVG. |
|---|---|---|---|
| 10 pg pBR322 | DH1 (1%) | 10,10 | 10 |
| | DH5 (1%) | 48,78 | 63 |
| 200 pg pXAD | DH1 (10%) | 11,13 | 12 |
| | DH5 (10%) | 205,185 | 195 |
| 1 ng p66 | DH1 (10%) | 1,1 | 1 |
| | DH5 (10%) | 34,26 | 30 |
| 1 ng pUC9 + cDNA | DH1 (10%) | 11,15 | 13 |
| | DH5 (10%) | 115,125 | 120 |
| 1 ng pUC8 + cDNA | DH1 (10%) | 24,24 | 24 |
| | DH5 (10%) | 240,260 | 250 |

EXAMPLE V

Tests were than performed to determine if the cells retained their enhanced tranformation properties after cold storage.

5×2.5ml colonies of the cells (DH1 or DH5), were mixed with 40 mls of SOB medium and grown to $OD_{550}$ of 0.6 DH1), and 0.48 (DH5).

$3 \times 10$ ml samples were then treated by centrifugation for 30 minutes on ice to obtain cell pellets. These pellets were then resuspended in one of the following media:
(A) SF: 10% glycerol, 10 μM KCH$_3$COO, 50 μM CaCl$_2$.2H$_2$O, 100 μM KCl at pH 6.1.
(B) RFT: 15% glycerol; 30 μM, KCH$_3$COO; 100 μM RbCl; 10 μM CaCl2.2H$_2$O; 50 μM MnCl2.4H$_2$O (pH 5.8).
(C) Frozen Storage Buffer (FSB)

| | | |
|---|---|---|
| KCl | 7.4 g | 100 mM |
| MnCl$_2$.4H$_2$O | 8.9 g | 45 mM |
| CaCl$_2$.2H$_2$O | 1.5 g | 10 mM |
| HACoCl$_3$ | 0.8 g | 3 mM |
| Potassium acetate | 10 ml of a 1 M stock (pH 7.5) | 10 mM |
| Redistilled glycerol (final pH 6.20 ± 0.10) | 100 g | 10% (w/v) |

These were kept on ice for 50 minutes, and then resuspended in the same medium. DMSO was added to FSB, and each sample was aliquoted into 5 nunc tubes, and flash frozen at −70° C.

Twenty four hours later, samples were thawed until just liquid, and then were mixed with samples of pBR322 (100pg), and incubated, followed by plating. The following results were obtained.

| | CFUs | AVG. |
|---|---|---|
| DH1 | | |
| SB | 10,8 | 9 |
| RB | 6,10 | 8 |
| FSB | 8,2 | 5 |
| DH5 | | |
| SB | 55,57 | 56 |
| RB | 52,48 | 47 |
| FSB | 34,40 | 37 |

Not only does DH5 transform at much higher frequencies than DH1, it also appears to remain more stable following storage than the cell line of choice, DH1.

As will be understood from the foregoing, especially Example I, the transformant used was an *E. coli* cell line which had been mutagenized by treatment with nitrosoguanadine and which contained the deoR mutant. These mutation appears to be key to the enhanced transformation frequency as DH1 and DH5 do not differ in any respect other than this. Additionally, comparison to other *E. coli* mutants, including ctyR and cytR +deoR shows that this ctyR mutation does not effect the transformation frequency of the cell line.

EXAMPLE VI

One skilled in the art will note immediately that while a specific chemical agent was used to obtain the deoR mutant used herein, additional chemical mutagens may be used to create the deoR mutation. Presence of the mutation can be determined in a given cell sample following the method set forth in Example I, supra, wherein growth on an inosine containing medium is seen to indicate its presence.

Additional methods of mutagenizing the *E. coli* cell line to obtain the desired deoR mutant cell line will be apparent to one skilled in the art. For example, both ultraviolet and X-irradiation may be used to produce mutations which may then be selected using the inosine containing medium described supra. Irradiation protocols may be found in, e.g., Miller, *Experiments in Molecular Genetics* (1972), (Cold Spring Harbor Laboratory, New York). Transposon insertional or deletional mutagenesis may be used as well. In this form of mutagenesis, transposons known to the art such as Tn5 and Tn10 can be inserted into the *E. coli* DNA, frequently with associated DNA deletions. Mutagenesis protocols may be found in, e.g., Davis et al., *Advanced Bacterial Genetics* (1980; Cold Spring harbor Laboratory, New York); Gilhavy et al., *Experiments With Gene Fusions* (1984; Cold Spring Harbor Laboratory, New York).

Spontaneous mutations to deoR can be selected and isolated by use of the inosine synthetic medium. While a low rate of mutation is to be expected ($\sim 10^{-7}$ cell/generation), this can be increased by inoculating about 50 ml of a cell sample to the SynIn medium described supra.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

I claim:
1. A biologically pure E. coli cell line which is characterized as deo R$^-$ mutant and by more efficient transformation with foreign plasmids than deo R$^+$ *E. coli* cell lines.
2. A biologically pure culture of deo R−mutant *E. coli* cell line DH5.
3. A method of obtaining a transformation efficient deo R$^-$ mutant cell line comprising,
    (a) mutating a deo R$^+$ *E. coli* cell sample;
    (b) culturing said sample on an inosine containing medium;
    (c) identifying colonies of deo R$^-$ mutants;
    (d) isolating said deo R$^-$ mutants from said sample;
    (e) transforming said isolated deo R$^-$ mutants and said deo R$^+$ cells with a plasmid; and,
    (f) selecting deo R$^-$ mutants which transform more efficiently than deo R$^+$ cells.
4. A method as in claim 3, wherein said cells are mutated by chemical means.
5. A method as in claim 4, wherein said chemical means comprise nitrosoguanidine.
6. A method as in claim 3, wherein said cells are mutated by irradiation.
7. A method as in claim 6, wherein said cells are mutated by ultraviolet or X irradiation.
8. A method as in claim 3, wherein said cells are mutated by genetic manipulation.
9. A method as in claim 8, wherein said cells are mutated by insertion of transposons.
10. A method as in claim 9, wherein said transposons are selected from the group consisting of Tn5 and Tn10.
11. The deo R$^-$ mutant E. coli cell line transformed with at least one foreign plasmid which contains a gene encoding a heterologous protein or polypeptide.
12. The cell line of claim 11, wherein said cell line is DH5.
13. Cell lines of claim 11, wherein said plasmid is selected from the group consisting of pBR322, pXAD, p66, pUC8, and pUC9.
14. A method of obtaining a protein comprising culturing the transformed *E. coli* cell line of claim 11 under conditions which promote expression of the heterologous protein encoded by said foreign plasmid.
15. A method as in claim 13, wherein said cell line is DH5.

* * * * *